US009310472B2

(12) United States Patent
Katsuyama

(10) Patent No.: US 9,310,472 B2
(45) Date of Patent: Apr. 12, 2016

(54) FOCAL POINT INFORMATION DETERMINATION METHOD AND APPARATUS, AND AMBIENT SOUND VELOCITY OBTAINING METHOD AND APPARATUS

(75) Inventor: Kimito Katsuyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 201 days.

(21) Appl. No.: 13/638,524

(22) PCT Filed: Mar. 31, 2011

(86) PCT No.: PCT/JP2011/001968
§ 371 (c)(1),
(2), (4) Date: Sep. 28, 2012

(87) PCT Pub. No.: WO2011/122049
PCT Pub. Date: Oct. 6, 2011

(65) Prior Publication Data
US 2013/0041262 A1 Feb. 14, 2013

(30) Foreign Application Priority Data

Mar. 31, 2010 (JP) ................. 2010-080595
Mar. 31, 2011 (JP) ................. 2011-078728

(51) Int. Cl.
*G01S 7/52* (2006.01)
*G01N 29/07* (2006.01)
*G10K 11/34* (2006.01)
*G01S 15/89* (2006.01)

(52) U.S. Cl.
CPC ............ *G01S 7/52049* (2013.01); *G01N 29/07* (2013.01); *G01S 15/8915* (2013.01); *G10K 11/346* (2013.01); *G01S 7/52074* (2013.01)

(58) Field of Classification Search
CPC .......... A61B 6/52; A61B 5/1128; A61B 8/00; A61B 8/52; G06T 7/0012; G01S 15/8906
See application file for complete search history.

(56) References Cited

U.S. PATENT DOCUMENTS

| 4,566,459 | A | * | 1/1986 | Umemura et al. | 600/443 |
| 6,508,768 | B1 | * | 1/2003 | Hall et al. | 600/443 |
| 6,958,041 | B2 | * | 10/2005 | Baba et al. | 600/443 |

(Continued)

FOREIGN PATENT DOCUMENTS

| CN | 102365054 A | 2/2012 |
| JP | 8-317926 A | 12/1996 |

(Continued)

OTHER PUBLICATIONS

Chinese Office Action in Chinese Patent Application No. 201180017570.6 Dated Apr. 30, 2014.

(Continued)

*Primary Examiner* — Tse Chen
*Assistant Examiner* — Nate S Sunwoo
(74) *Attorney, Agent, or Firm* — Sughrue Mion, PLLC

(57) ABSTRACT

Transmitting an ultrasonic wave focused on a predetermined transmit focus position by driving each of the elements of the ultrasonic probe based on a predetermined transmit delay time, and determining a true focal position of the ultrasonic wave transmitted to the transmit focus position or a focal point valid region that includes the true focal position based on a receive signal received by each element according to a reflection wave reflected by the transmission of the ultrasonic wave to the transmit focus position.

12 Claims, 10 Drawing Sheets

(56) References Cited

U.S. PATENT DOCUMENTS

| | | | |
|---|---|---|---|
| 2009/0003128 A1* | 1/2009 | Jeong et al. | 367/7 |
| 2009/0093721 A1 | 4/2009 | Katsuyama | |
| 2009/0099455 A1* | 4/2009 | Katsuyama | 600/459 |
| 2012/0078105 A1 | 3/2012 | Kamiyama | |

FOREIGN PATENT DOCUMENTS

| | | | |
|---|---|---|---|
| JP | 2007-7045 A | | 1/2007 |
| JP | 2007007045 A | * | 1/2007 |
| JP | 2009-101145 A | | 5/2009 |
| JP | 2009-261520 A | | 11/2009 |
| JP | 2009261520 A | * | 11/2009 |
| WO | 2007075040 A1 | | 7/2007 |

OTHER PUBLICATIONS

Communication dated Sep. 22, 2014 from the European Patent Office in counterpart European Patent Application No. 11762290.2.

* cited by examiner

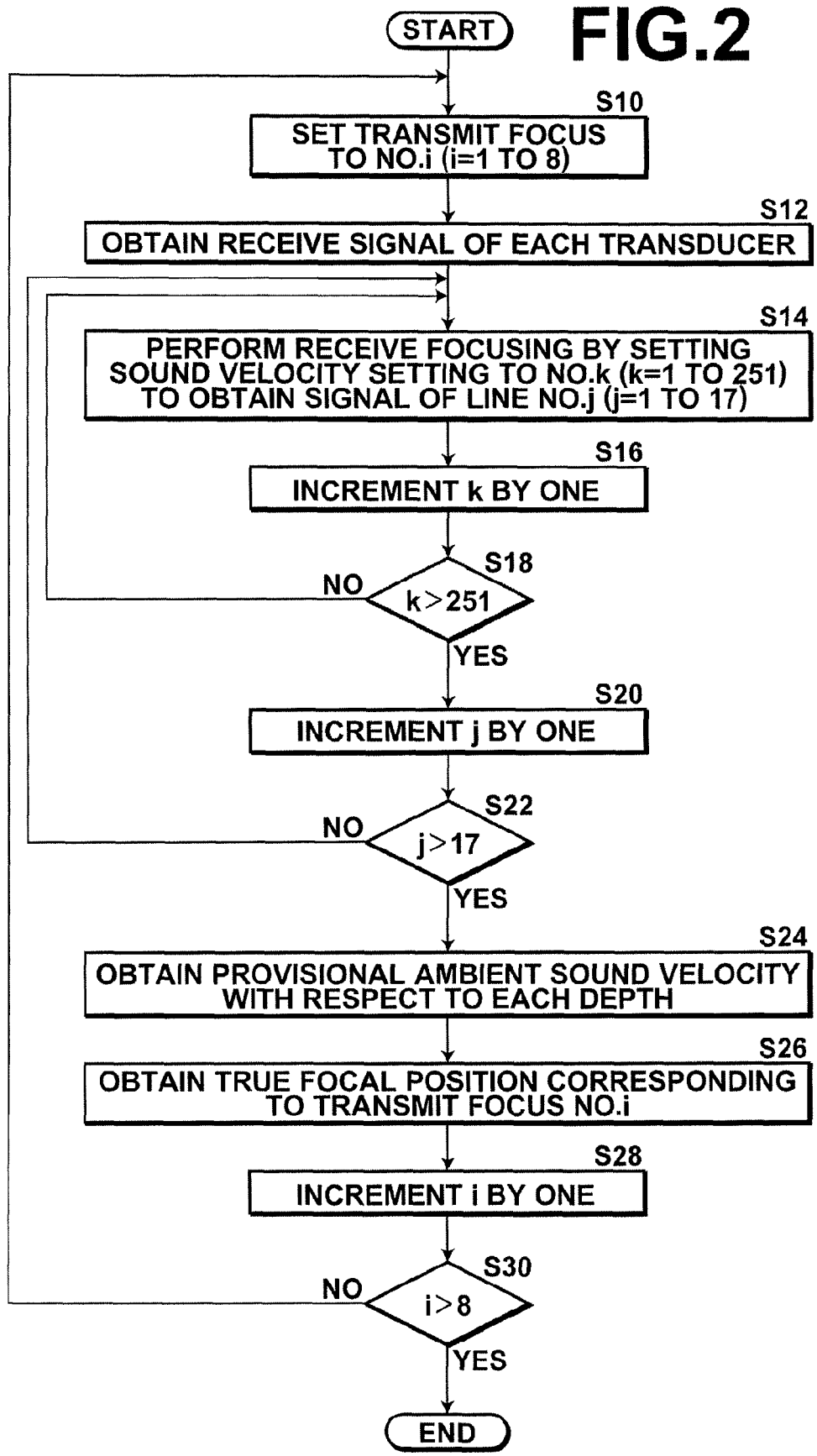

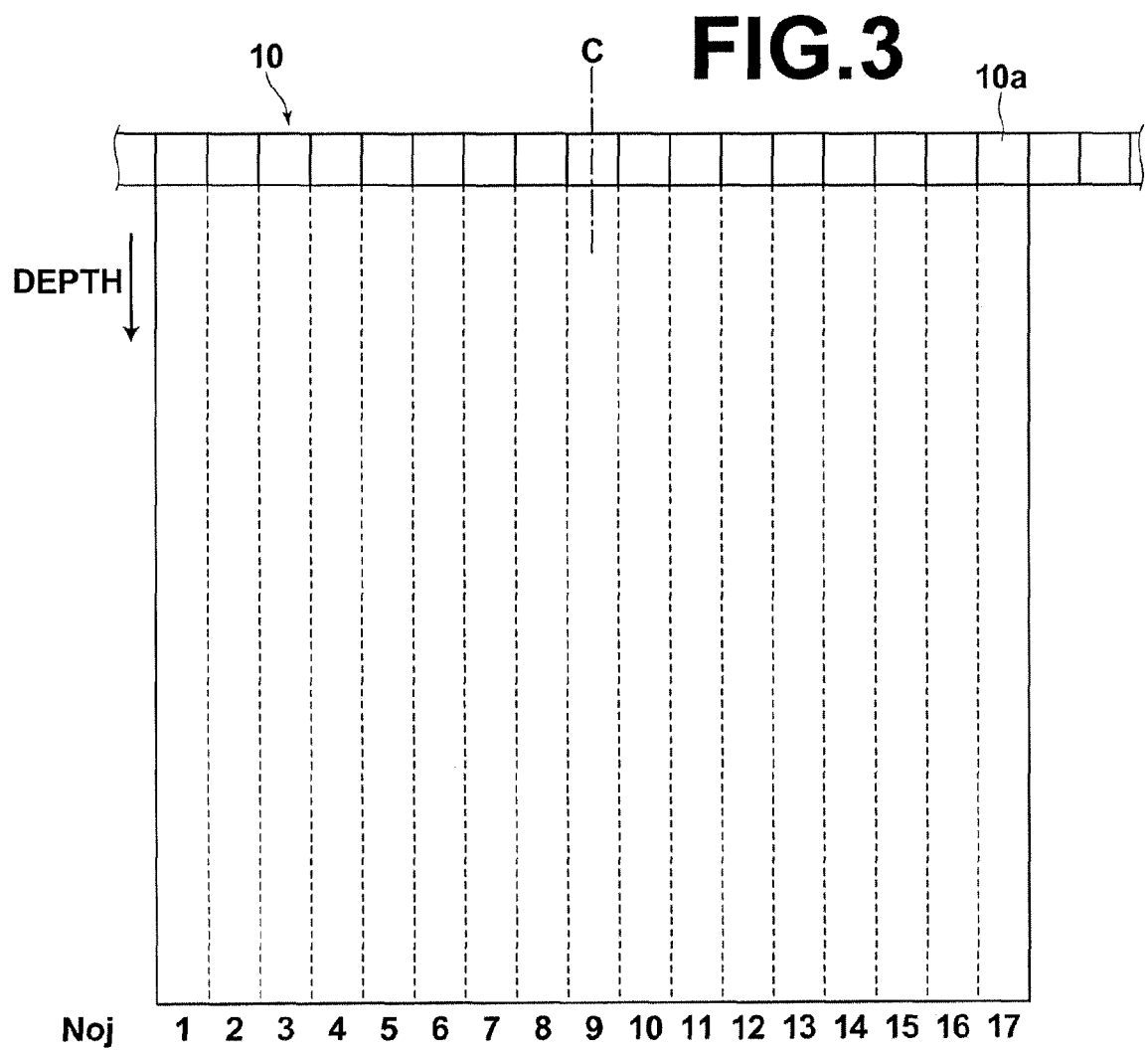
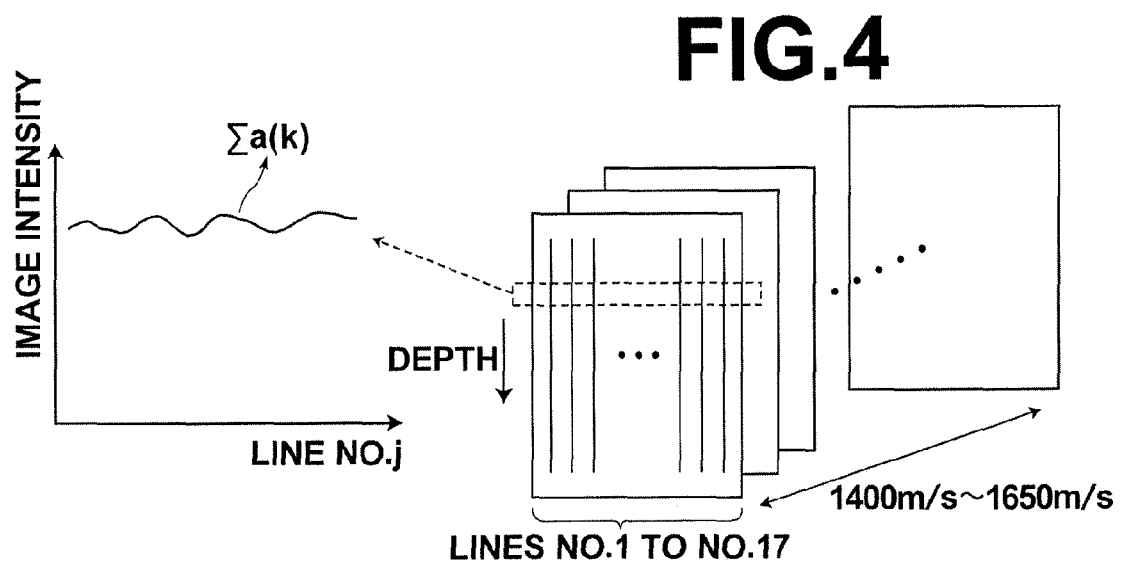

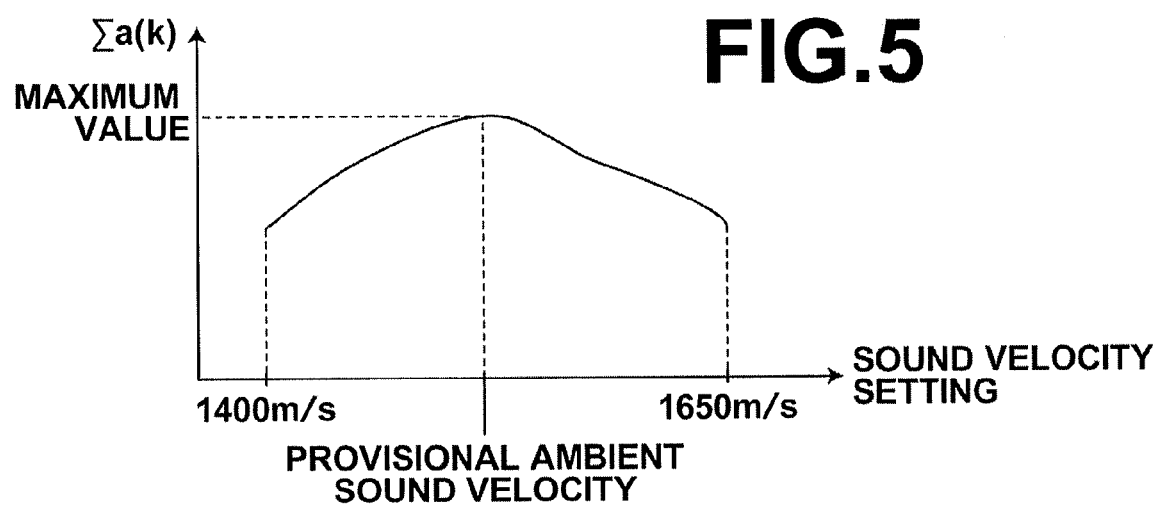

FIG.6
TRANSMIT FOCUS No.1=12mm 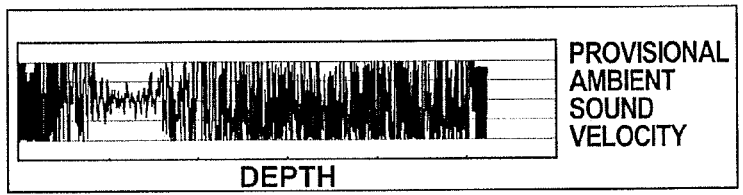
TRANSMIT FOCUS No.2=16mm 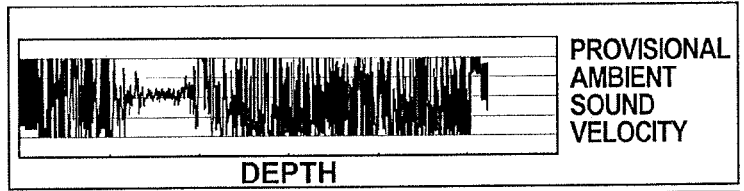
TRANSMIT FOCUS No.3=20mm 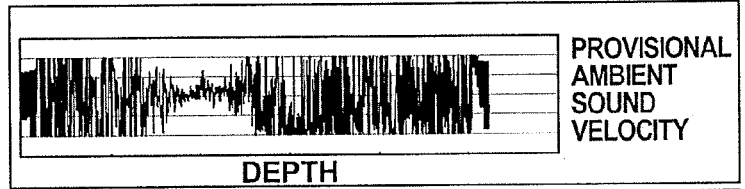
TRANSMIT FOCUS No.4=24mm 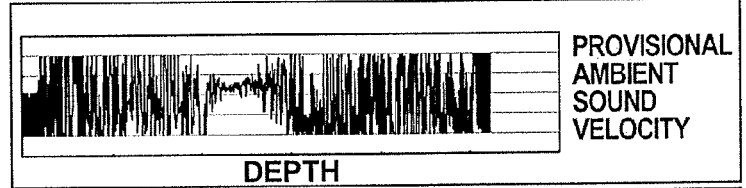
TRANSMIT FOCUS No.5=28mm 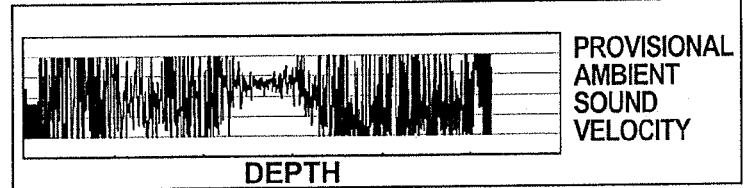
TRANSMIT FOCUS No.6=32mm 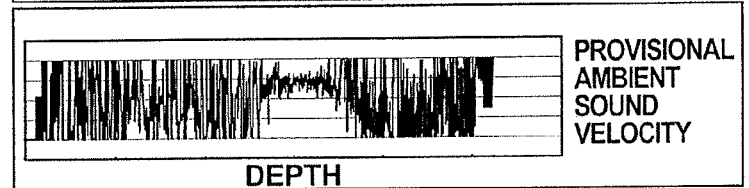
TRANSMIT FOCUS No.7=36mm 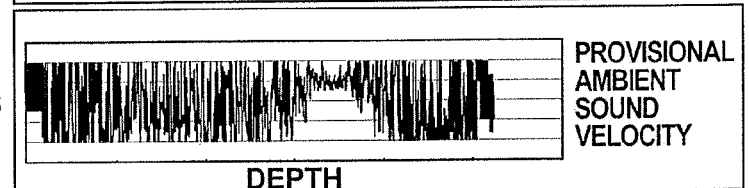
TRANSMIT FOCUS No.8=40mm 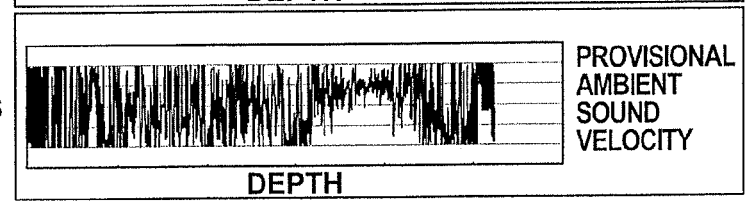

FOCAL POINT INFORMATION DETERMINATION METHOD AND APPARATUS, AND AMBIENT SOUND VELOCITY OBTAINING METHOD AND APPARATUS

CROSS REFERENCE TO RELATED APPLICATIONS

This application is a National Stage of International Application No. PCT/JP2011/001968 filed Mar. 31, 2011, claiming priority based on Japanese Patent Application Nos. 2010-080595 filed Mar. 31, 2010 and 2011-078728 filed Mar. 31,2011, the contents of all of which are incorporated herein by reference in their entirety.

TECHNICAL FIELD

The present invention relates generally to an ultrasonic diagnostic apparatus and more specifically to a focal point information determination method and apparatus for determining a true focal position of ultrasonic waves transmitted from an ultrasonic probe or a valid region in which the true focal position is present. The invention also relates to an ambient sound velocity obtaining method and apparatus.

BACKGROUND ART

Ultrasonic diagnostic apparatuses for obtaining a tomographic image of a subject using ultrasonic waves for medical diagnosis have been proposed. In such an ultrasonic diagnostic apparatus, when transmitting ultrasonic waves from an ultrasonic probe, so-called transmit focusing in which a transmit delay time is set to each ultrasonic wave transmitted from each element of the ultrasonic probe is performed and when obtaining receive signals, so-called receive focusing in which a receive time delay is set to each signal received by each element is performed in order to improve azimuth resolution.

When such transmit focusing and receive focusing are carried out, a representative sound velocity of the diagnostic target region is assumed and transmit delay times and receive delay times are set based on the assumed sound velocity.

But, the ambient sound velocity of a subject is not constant and differs from tissue to tissue, and if the assumed sound velocity differs from the ambient sound velocity, a problem of image quality degradation may arise.

One reason for image quality degradation is that the transmit delay times of transmit focusing or receive delay times of receive focusing differ from the transmit delay times for properly forming a transmit focal point on a target or receiving times of ultrasonic waves reflected from the target and received by the respective elements of the ultrasonic probe.

The term "ambient sound velocity" as used herein refers to a sound velocity determined based on the distance from a predetermined target to each element and the receiving time of each element when the ultrasonic wave is transmitted to the target.

Attempts have been made to prevent the image quality degradation by matching the assumed sound velocity with the ambient sound velocity.

For example, Japanese Unexamined Patent Publication No. 2007-007045 proposes the following. First, ultrasonic waves delayed so as to converge at a focal point T are transmitted from an opening having a predetermined width centered on the predetermined center of the opening at a normal sound velocity setting.

Then, reflection waves are received by all elements of the ultrasonic probe and receive focusing is performed on the signals with respect to focal points P1 and P2 at different sound velocity settings to generate a beam profile with respect to each sound velocity setting corresponding to each focal point.

Then, a beam profile having a smallest half width of the beam profiles of the respective focal points is selected, and the sound velocity setting corresponding to the selected beam profile is assumed to be the ambient sound velocity of the region of the subject.

In the method described in Japanese Unexamined Patent Publication No. 2007-007045, if the receive focal points P1, P2 are viewed as the attention points for obtaining ambient sound velocities, each of the attention points differs from the transmit focal point T in depth. In the case where the attention points are located adjacent to the focal point T, the ambient sound velocity may be obtained with satisfactory accuracy, but as the distance between them becomes large, the accuracy of the ambient sound velocity is degraded. In the case of speckle, in particular, the accuracy is degraded significantly due to interference from around the attention point and sometimes there may be a case that the ambient sound velocity cannot be obtained.

Further, in the method described in Japanese Unexamined Patent Publication No. 2007-007045, if the ambient sound velocity differs from the sound velocity setting, the transmit focal point differs from the transmit focal point T in depth as the transmit focal point T is at a depth where the ultrasonic waves converges at a normal setting sound velocity. In this case, the distance between the attention point and transmit focal point becomes large and the accuracy of ambient sound velocity is largely degraded so that sometimes there may be a case that the ambient sound velocity cannot be obtained.

Further, even if the attention points are located adjacent to the transmit focal point T, a correct ambient sound velocity may not be sometimes obtained due to interference. That is, the transmission wavefront becomes like that illustrated in FIG. 11 adjacent to the focal point, but a reflected wavefront identical to the transmission wavefront is falsely formed due to reflections from countless scattering points in each depth, resulting in an error in the ambient sound velocity obtained. More specifically, as illustrated in FIG. 11, the ambient sound velocity becomes fast in a region shallower than the transmit focal point and slow in a region deeper than the transmit focal point. FIG. 12 is a graph illustrating the ambient sound velocity with respect to the depth in the case where the error in the ambient sound velocity described above occurs.

In order to solve the problem, a method in which sound velocity setting of the transmit focus is changed, as well as the receive focus, with respect to the attention point is conceivable. But it requires a huge number of transmission times to change the sound velocity setting and transmits the ultrasonic waves each time the setting is changed. This takes too much time to obtain the ambient sound velocity, resulting in degradation in the processing or diagnostic efficiency.

The present invention has been developed in view of the circumstances described above and it is an object of the present invention to provide a focal point information determination method and apparatus and an ambient sound velocity obtaining method and apparatus capable of obtaining an ambient sound velocity successfully without causing degradation in the processing or diagnostic efficiency.

Disclosure of Invention

A focal point information determination method is a method which uses an ultrasonic probe having a plurality of elements disposed therein, each for transmitting an ultrasonic wave into a subject and outputting a receive signal by receiving a reflection wave reflected from the subject by the transmission of the ultrasonic wave, wherein the method comprises:

a transmission step for transmitting the ultrasonic wave focused on a predetermined transmit focus position by driving each of the elements of the ultrasonic probe based on a predetermined transmit delay time; and a determination step for determining a true focal position of the ultrasonic wave transmitted to the transmit focus position or a focal point valid region that includes the true focal position based on a receive signal received by each element according to a reflection wave reflected by the transmission of the ultrasonic wave to the transmit focus position.

In the focal point information determination method of the present invention described above, the determination step may include the steps of:

performing receive focusing on the receive signals corresponding to the transmit focus position using receive delay times calculated based on a plurality of sound velocity settings to obtain line image signals extending in a depth direction of the subject with respect to each of the sound velocity settings;

obtaining a provisional ambient sound velocity distribution in the depth direction of the subject based on the line image signals with respect to each of the sound velocity settings; and determining the true focal position or the focal point valid region that includes the true focal position based on the obtained provisional ambient sound velocity distribution.

Further, the true focal position or the focal point valid region may be determined by a variation of the provisional ambient sound velocity distribution.

Still further, a depth where the variation of the provisional ambient sound velocity becomes minimal may be obtained as the true focal position.

Further, the transmission step may be a step in which the ultrasonic wave focused on a plurality of transmit focus positions is transmitted with respect to each transmit focus position, and the determination step may be a step in which a true focal position of the ultrasonic wave transmitted to each transmit focus position is determined based on a receive signal received by the transmission of the ultrasonic wave to each transmit focus position.

An ambient sound velocity obtaining method of the present invention is a method for obtaining an ambient sound velocity of any arbitrary attention point in the subject based on the true focal position or the focal point valid region that includes the true focal position determined by the focal point information determination method described above.

Another ambient sound velocity obtaining method of the present invention is a method for obtaining an ambient sound velocity of any arbitrary attention point in the subject based on a receive signal, the ambient sound velocity obtained by transmitting the ultrasonic wave to a transmit focus position corresponding to each of the plurality of true focal positions, the true focal postitions determined by the focal point information determination method described above.

Still another ambient sound velocity obtaining method of the present invention is a method for obtaining an ambient sound velocity of any arbitrary attention point in the subject based on the focal position or the focal point valid region that includes the true focal position, the true focal position determined by the focal point information determination method described above, wherein a range of the line image signals in the depth direction used for obtaining the provisional ambient sound velocity is narrower than a range of the line image signals in the depth direction used for obtaining the ambient sound velocity.

A focal point information determination apparatus of the present invention is an apparatus, including:

an ultrasonic probe having a plurality of elements disposed therein, each for transmitting an ultrasonic wave into a subject and outputting a receive signal by receiving a reflection wave reflected from the subject by the transmission of the ultrasonic wave;

a transmission control section for transmitting the ultrasonic wave focused on a predetermined transmit focus position by driving each of the elements of the ultrasonic probe based on a predetermined transmit delay time; and a focal point information determination section for determining a true focal position of the ultrasonic wave transmitted to the transmit focus position or a focal point valid region that includes the true focal position based on a receive signal received by each element according to a reflection wave reflected by the transmission of the ultrasonic wave to the transmit focus position.

The focal point information determination apparatus of the present invention described above may further include a receiving control section for performing receive focusing on the receive signals corresponding to the transmit focus position using receive delay times calculated based on a plurality of sound velocity settings to obtain line image signals extending in a depth direction of the subject with respect to each of the sound velocity settings, and the focal point information determination section may be a section that obtains a provisional ambient sound velocity distribution in the depth direction of the subject based on the line image signals with respect to each of the sound velocity settings and determines the true focal position or the focal point valid region based on the obtained provisional ambient sound velocity distribution.

Further, the focal point information determination section may be a section that determines the true focal position or the focal point valid region based on a variation of the provisional ambient sound velocity distribution.

Still further, the focal point information determination section may be a section that obtains a depth where the variation of the provisional ambient sound velocity becomes minimal as the true focal position.

Further, the transmission control section may be a section that transmits the ultrasonic wave focused on a plurality of transmit focus positions with respect to each transmit focus position, and the focal point information determination section may be a section that determines a true focal position of the ultrasonic wave transmitted to each of the transmit focus positions.

An ambient sound velocity obtaining apparatus of the present invention is an apparatus, including:

the focal point information determination apparatus described above; and an ambient sound velocity obtaining section for obtaining an ambient sound velocity of any arbitrary attention point in the subject based on the true focal position or the focal point valid region that includes the true focal position determined by the focal point information determination apparatus.

Another ambient sound velocity obtaining apparatus of the present invention is an apparatus, including:

the focal point information determination apparatus described above; and an ambient sound velocity obtaining section for obtaining an ambient sound velocity of any arbitrary attention point in the subject based on a receive signal obtained by transmitting the ultrasonic wave to a transmit focus position corresponding to each of the plurality of true focal positions determined by the focal point information determination apparatus.

Still another ambient sound velocity obtaining apparatus of the present invention is an apparatus, including:

the focal point information determination apparatus described above; and an ambient sound velocity obtaining section for obtaining an ambient sound velocity of any arbitrary attention point in the subject based on the true focal position or the focal point valid region that includes the true focal position determined by the focal point information determination apparatus, wherein a range of the line image signals in the depth direction used for obtaining the provisional ambient sound velocity by the focal point information determination section is narrower than a range of the line image signals in the depth direction used for obtaining the ambient sound velocity by the ambient sound velocity obtaining section.

The ambient sound velocity obtaining apparatuses described above may further include an attention point input section for receiving an input specifying any arbitrary attention point.

Further, the ambient sound velocity obtaining apparatuses described above may further include a receiving control section for generating an ultrasonic image signal using a receive delay time calculated based on the ambient sound velocity obtained by the ambient sound velocity obtaining section.

According to the focal point information determination method and apparatus, and the ambient sound velocity obtaining method and apparatus of the present invention, an ultrasonic wave focused on a plurality of transmit focus positions is transmitted with respect to each transmit focus position by driving each of the elements of the ultrasonic probe based on a predetermined transmit delay time and a true focal position of the ultrasonic waves transmitted to the transmit focus position or a focal point valid region that includes the true focal position, the true focal position being determined with respect to each transmit focus position based on a receive signal received by each element according to a reflection wave reflected by the transmission of the ultrasonic wave to each transmit focus position. This allows the ambient sound velocity of any arbitrary attention point in a subject to be obtained with high accuracy based on the receive signal received, the receive signal received according to the transmission of the ultrasonic wave to a transmit focus position corresponding to the range that includes the arbitrary attention point.

Further, it is not required to change the sound velocity setting of the transmission focus and transmit ultrasonic wave each time the setting is changed so that an ambient sound velocity may be obtained in a short time.

BRIEF DESCRIPTION OF DRAWINGS

FIG. 2 is a flowchart, illustrating a valid region determination method in an embodiment of the ultrasonic diagnostic apparatus of the present invention.

FIG. 3 illustrates lines used for determining a valid region.

FIG. 4 illustrates the valid region determination method.

FIG. 5 illustrates the valid region determination method.

FIG. 6 illustrates an ambient sound velocity distribution in a depth direction with respect to each transmit focus position.

BEST MODE FOR CARRYING OUT THE INVENTION

Figure 1:
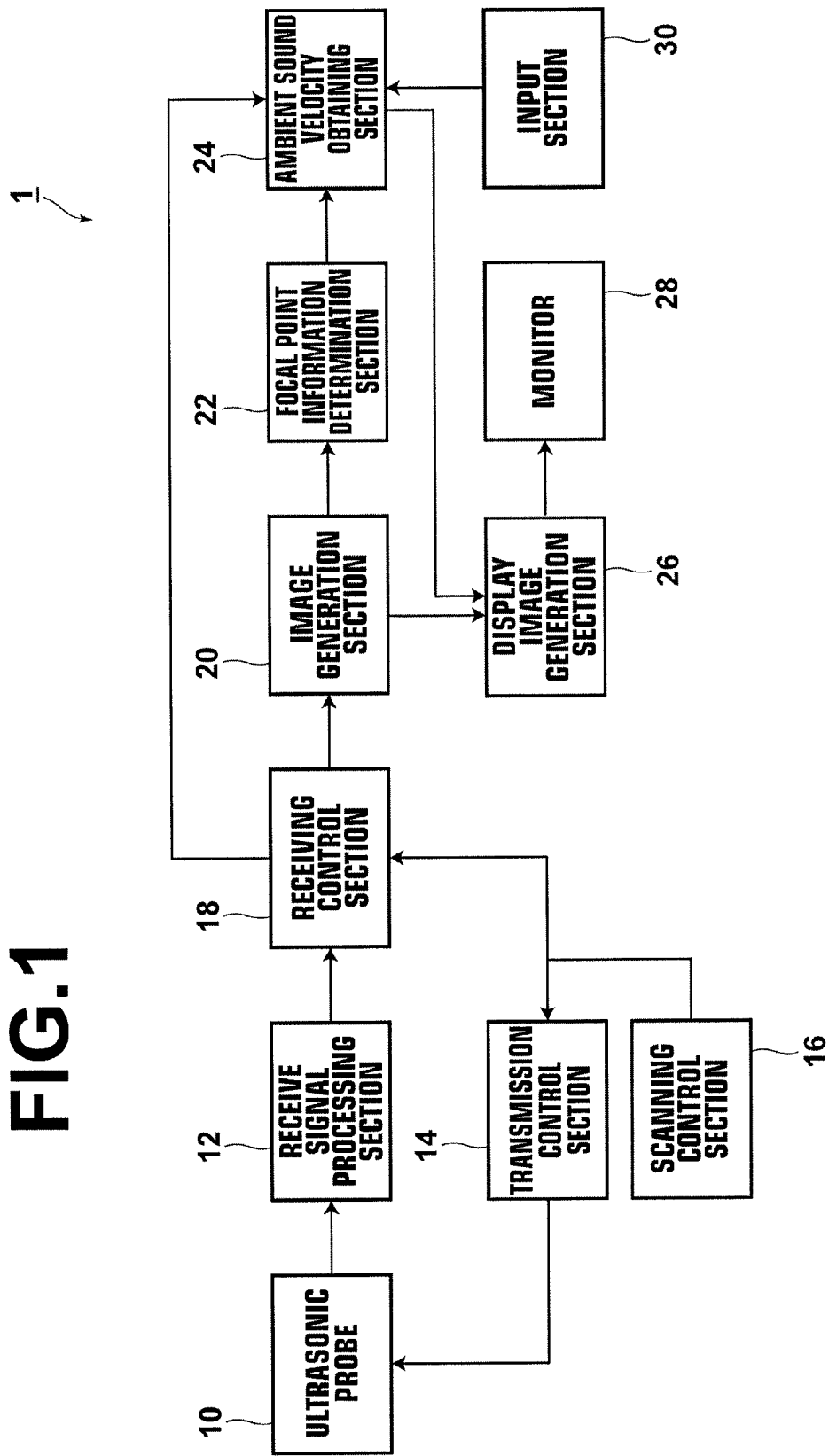
FIG. 1 is a block diagram of an embodiment of the ultrasonic diagnostic apparatus of the present invention, illustrating a schematic configuration thereof.

Hereinafter, an embodiment of the ultrasonic diagnostic apparatus the present invention will be described in detail with reference to the accompanying drawings. FIG. 1 is a block diagram of the ultrasonic diagnostic apparatus of the present embodiment, illustrating a schematic configuration thereof.

As shown in FIG. 1, the ultrasonic diagnostic apparatus 1 of the present embodiment includes an ultrasonic probe 10, a receive signal processing section 12, a transmission control section 14, a scanning control section 16, a receiving control section 18, an image generation section 20, a focal point information determination section 22, an ambient sound velocity obtaining section 24, a display image generation section 26, a monitor 28, and an input section 30.

The ultrasonic probe 10 is a probe for transmitting an ultrasonic wave toward a diagnostic target region in a subject body and receiving an ultrasonic wave reflected from inside of the body. The ultrasonic probe 10 of the present embodiment includes a plurality of ultrasonic transducers forming a one-dimensional ultrasonic transducer array, and each ultrasonic transducer is a vibrator formed, for example, of a piezoelectric element, such as a PZT or the like, with an electrode formed on each side. The electrodes are connected to the receive signal processing section 12 and transmission control section 14 by signal wires. A voltage according to a drive pulse voltage signal outputted from the transmission control section 14 is applied between the electrodes, and the vibrator generates an ultrasonic wave according to the applied voltage. Further, the vibrator generates an electrical signal upon receipt of a reflected ultrasonic wave and outputs the electrical signal to the receive signal processing section 12 as the receive signal.

The transmission control section 14 causes an ultrasonic wave that will converge at a predetermined focus to be outputted from the ultrasonic probe 10 by outputting a drive pulse voltage signal to each ultrasonic transducer of the ultrasonic probe 10 based on a transmit delay time outputted from the scanning control section 16 and causing the vibrator of each ultrasonic transducer to transmit an ultrasonic wave according to the transmit delay time.

The receive signal processing section 12 includes a plurality of amplifiers and A/D converters, each pair of the amplifier and A/D converter corresponding to each transducer of the ultrasonic probe 10. The receive signal outputted from each ultrasonic transducer is amplified by the amplifier, then the analog receive signal outputted from the amplifier is converted to a digital receive signal by the A/D converter, and the digital receive signal is outputted to the receiving control section 18.

The receiving control section 18 outputs an in-phase sum signal of narrowly focused ultrasonic echo by performing receive focusing on a plurality of receive signals outputted from a plurality of ultrasonic transducers of the ultrasonic probe 10 based on predetermined receive delay times. The receive delay times are set based on the sound velocity in a subject and the setting method will be describe in detail later.

The scanning control section 16 controls transmit focusing and receive focusing by outputting transmit delay times and receive delay times to the transmission control section 14 and receiving control section 18 respectively.

The image generation section 20 generates an ultrasonic image signal representing tomographic image information of a tissue in a subject based on the in-phase sum signal outputted from the receiving control section 18.

The focal point information determination section 22 determines, based on receive signals obtained according to ultrasonic waves transmitted from the ultrasonic probe 10 by focusing the waves on a predetermined position of transmit focus, a true focal position or a valid region that includes the true focal position. The method for determining the focus position or valid region that includes the true focal position will be described in detail later.

The ambient sound velocity obtaining section 24 obtains, with respect to an arbitrary attention point in a subject, a focus position adjacent to the attention point or a valid region in which the attention point presents and obtains the ambient sound velocity of the attention point based on receive signals obtained according to ultrasonic waves transmitted to a transmit focus position corresponding to the focal position or the valid region. The method for obtaining the ambient sound velocity will be described in detail later.

The display image generation section 26 generates a display control signal based on the ultrasonic image signal outputted from the image generation unit 20 and outputs the generated display control signal to the monitor 28.

The monitor 28 displays an ultrasonic image of a subject based on the inputted display control signal or the ambient sound velocity of the arbitrary attention point obtained by the ambient sound velocity obtaining section 24 as a numerical value.

The input section 30 receives input of various imaging conditions and operator instructions and includes a pointing device such as a keyboard and mouse. In the present embodiment, the input section 30 corresponds to the attention point input section recited in claim 36.

An operation of the ultrasonic diagnostic apparatus of the present embodiment will now be described. The ultrasonic diagnostic apparatus of the present embodiment is designed, when an arbitrary point is specified by the operation in a displayed ultrasonic image in a subject, to obtain and display the ambient sound velocity with respect to the attention point. But, an operation for displaying an ultrasonic image in a subject will be described first.

First, a drive pulse voltage signal is outputted from the transmission control section 14 to each ultrasonic transducer of the ultrasonic probe 10 based on a control signal according to a transmit delay time outputted from the scanning control section 16. Here, a different transmit delay time is set to each drive pulse voltage signal such that the ultrasonic wave transmitted from each ultrasonic transducer converges at a preset focal point. The transmit delay times are values calculated in advance based on an assumed sound velocity setting set by assuming ambient sound velocity in the subject.

Then, the vibrator of each ultrasonic transducer of the ultrasonic probe 10 vibrates mechanically by receiving the drive pulse voltage signal described above, whereby an ultrasonic wave is generated and transmitted to the subject.

The ultrasonic wave transmitted from each ultrasonic transducer propagates in the subject and is reflected successively at discontinuity surfaces of acoustic impedance and the echo of the reflection is detected by each ultrasonic transducer and the vibrator vibrates. This vibration causes a weak electrical signal to be generated from the vibrator of each ultrasonic transducer and the electrical signal is outputted to the receive signal processing section 12 as the receive signal.

In the receive signal processing section 12, the receive signal outputted from each ultrasonic transducer is amplified by the amplifier and the amplified signal is converted to a digital receive signal by the A/D converter and the digital receive signal is outputted to receiving control section 18.

In the receiving control section 18, receive focusing is performed on a plurality of receive signal outputted from a plurality of ultrasonic transducers based on predetermined receive delay times outputted from the scanning control section 16 and an in-phase sum signal is generated. The receive delay times outputted from the scanning control section 16 are values calculated based on an assumed sound velocity setting set by assuming ambient sound velocity in the subject in advance such that the in-phase sum signal corresponds to the signal presented at a predetermined focal point in the subject.

Then, by controlling the receive delay times outputted from the scanning control section 16, an in-phase sum signal of each focal point within the imaging range in the subject is obtained by the receiving control section 18 and the in-phase sum signals are sequentially outputted to the image generation section 20.

The image generation section 20 stores the inputted in-phase sum signals in series, then generates an ultrasonic image signal representing tomographic image information of the subject, and outputs the ultrasonic image signal to the display image generation section 26.

In the display image generation section 26, a display control signal is generated based on the inputted ultrasonic image signal and the display control signal is outputted to the monitor 28. The monitor 28 displays an ultrasonic image of the subject based on the inputted display control signal.

Thereafter, the ultrasonic wave transmission from each ultrasonic transducer of the ultrasonic probe 10 is carried out according to a predetermined frame rate, and the aforementioned steps are repeated to display an ultrasonic image at the predetermined frame rate in succession.

So far the operation of the ultrasonic diagnostic apparatus of the present embodiment for displaying an ultrasonic image has been described.

Next, an operation for obtaining and displaying the ambient sound velocity of an attention point specified by the operator while an ultrasonic image in a subject like that described above is displayed will be described.

First, a given attention point is specified by the operator using the input section 30 in an ultrasonic image displayed on the monitor. When an instruction signal to display the ambient sound velocity of the attention point is received by the input section 30 from the operator, the steps of the flowchart shown in FIG. 2 are performed.

More specifically, the transmit focus of ultrasonic waves transmitted from the ultrasonic probe 10 is set to a predetermined position No. 1 and drive pulse voltage signals based on the transmit delay times according to the position No. 1 are outputted from the transmission control section 14 and an ultrasonic wave is transmitted from each transducer of the ultrasonic probe 10 (S10). Note that the transmit delay times here are values calculated in advance based on an assumed sound velocity setting set by assuming an ambient sound velocity in the subject.

In the present embodiment, as transmit focus No. i, No. 1 to No. 8 are preset in the scanning control section 16. More specifically, they are set at the following depths: No. 1=12 mm, No. 2=16 mm, No. 3=20 mm, No. 4=24 mm, No. 5=28 mm, No. 6=32 mm, No. 7=36 mm, and No. 8=40 mm.

Then an echo due to reflection of the ultrasonic wave transmitted from each ultrasonic transducer is detected by each ultrasonic transducer, and the receive signal is outputted to the receive signal processing section 12 where the signal is subjected to amplification and A/D conversion before being outputted to the receiving control section 18 (S12).

The receiving control section 18 performs receive focusing on the receive signals using receive delay times calculated based on a predetermined sound velocity setting No. 1 and calculates in-phase sum signals for a line No. 1 and outputs the signals to the image generation section 20 (S14).

In the present embodiment, as sound velocity setting No. k for calculating receive delay times, No. 1 to No. 251 are preset in the scanning control section 16. More specifically, the sound velocity settings No. 1 to No. 251 are from 1400 m/s to 1650 m/s and each sound velocity setting is set at an increment of 1 m/s. The scanning control section 16 calculates receive delay times based on the sound velocity settings and outputs the calculated receive delay times to the receiving control section 18.

Further, as line No. j, lines No. 1 to No. 17 are allocated to ±8 lines centered on the ultrasonic transducer 10a at the prescribed center of opening C of the ultrasonic probe 10, as shown in FIG. 3.

Next, the receiving control section 18 changes the receive delay times to those calculated based on the sound velocity setting No. 2 (S16, S18). Then, the receiving control section 18 performs receive focusing on the receive signals using the changed receive delay times to calculate the in-phase sum signal for the line No. 1 again and outputs the signal to the image generation section 20 (S14).

With respect to the line No. 1, the receiving control section 18 obtains an in-phase sum signal subjected to the receive focusing with the receive delay times based on each of the sound velocity settings of 1400 m/s to 1650 m/s by repeating the steps from S14 to S18, then further performs envelope detection, and outputs the results to the image generation section 20.

That is, the image generation section 20 obtains a line image signal for each of the sound velocity settings of 1400 m/s to 1650 m/s corresponding to the line No. 1.

Next, the receiving control section 18 changes the target line for receive focusing from the line No. 1 to line No. 2 (S20). Then, with respect to the line No. 2, the steps S14 to S18 are repeated by the receiving control section 18, whereby a line image signal for each of the sound velocity settings of 1400 m/s to 1650 m/s corresponding to the line No. 2 is obtained by the image generation section 20.

Thereafter, with respect to lines No. 3 to No. 17, the steps from S14 to S18 are repeated (S22), whereby a line image signal for each of the sound velocity settings of 1400 m/s to 1650 m/s corresponding to each of the lines No. 3 to No. 17 is obtained by the image generation section 20.

In this way, an ultrasonic image signal constituted by line image signals of lines No. 1 to No. 17 is generated with respect to each of the sound velocity settings of 1400 m/s to 1650 m/s, as illustrated in FIG. 4, and obtained by the image generation section 20.

The image generation section 20 outputs the ultrasonic image signal with respect to each of the sound velocity settings of 1400 m/s to 1650 m/s to the focal point information determination section 22. The focal point information determination section 22 calculates a provisional ambient sound velocity with respect to each unit depth of the subject based on the inputted ultrasonic image signal with respect to each sound velocity setting (S24).

More specifically, an image intensity distribution with respect to each line for a predetermined unit depth (indicated by a dotted rectangle) is obtained with respect to the ultrasonic image signal of each sound velocity setting, as illustrated on the left side of FIG. 4 and sum Σa (k) of the image intensity with respect to each line is calculated. By way of example, the unit depth is 20 μm to 50 μm. The unit depth is smaller than the depth used for obtaining an ambient sound velocity, to be described later. The use of the provisional ambient sound velocity based on an image intensity of local narrow range allows a change with respect to the depth may be captured highly accurately as an ambient sound velocity not affected by image intensities of other depths. Further, the provisional ambient sound velocity may be obtained in a short time.

Then, as illustrated in FIG. 5, a distribution of the sum Σa (k) with respect to each of the sound velocity settings of 1400 m/s to 1650 m/s is obtained, then a maximum value of all the sums Σa (k) is obtained, and a sound velocity setting corresponding to the maximum value is obtained as the provisional ambient sound velocity of the subject.

Similar processing is performed by changing the depth and a provisional ambient sound velocity with respect to each unit depth is obtained, whereby a provisional ambient sound velocity distribution with respect to the depth corresponding to the transmit focus No. 1 illustrated at the top of FIG. 6 is obtained.

Then, a variation in the provisional ambient sound velocities with respect to the depth is measured by obtaining a provisional ambient sound velocity with respect to each unit depth. More specifically, in the provisional ambient sound velocity distributions shown in FIG. 6, for example, a predetermined calculation window is sequentially scanned in the depth direction to sequentially obtain a standard deviation of the provisional ambient sound velocities within the calculation window, whereby the distribution of standard deviations with respect to the depth shown in FIG. 7 may be obtained. Note that the leftmost graph in FIG. 7 is the distribution of standard deviations of the provisional ambient sound velocities when the transmit focus is set to No. 1=12 mm.

Figure 7:
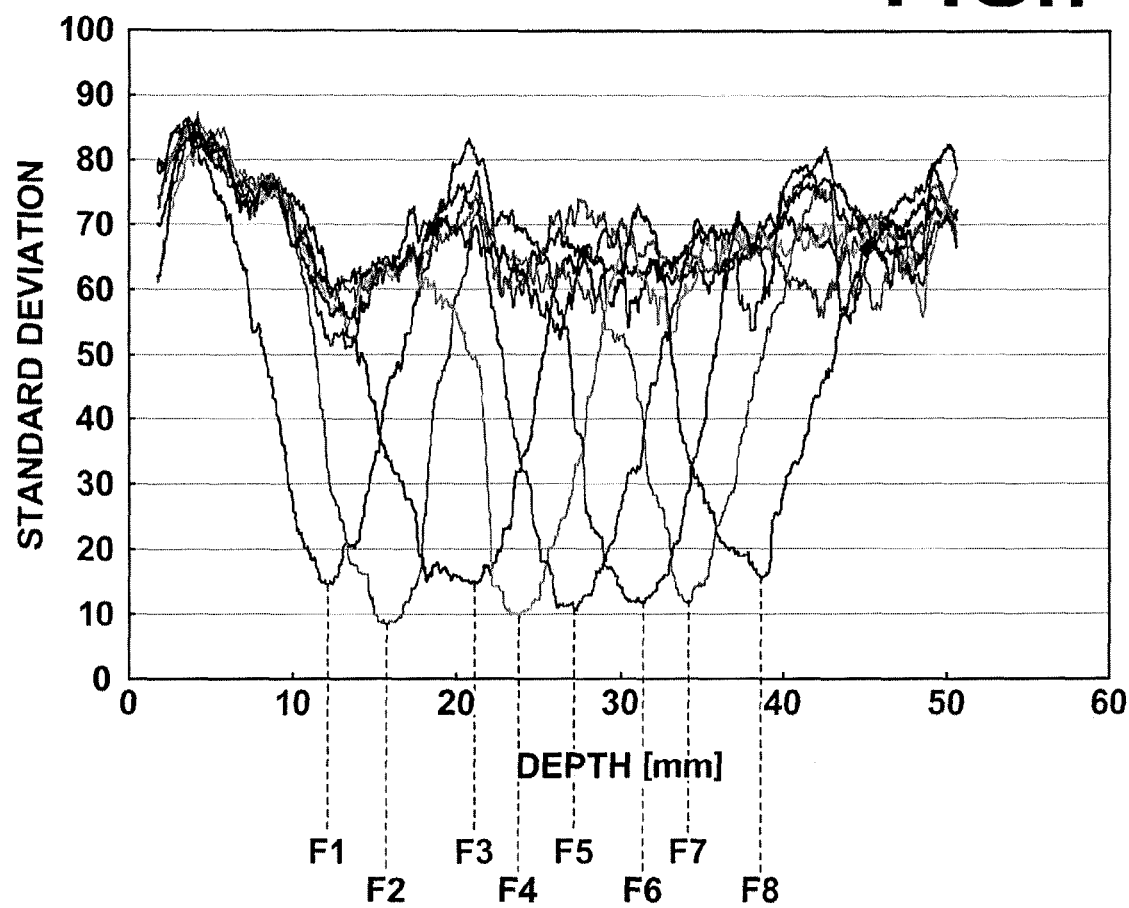
FIG. 7 illustrates a standard deviation of the ambient sound velocity distribution with respect to each transmit focus position.

Then, a depth F1 where the standard deviation of the provisional ambient sound velocities with respect to the depth is minimal, as shown in FIG. 7, is obtained as the true focal position of the ultrasonic wave corresponding to the transmit focus No. 1 (S26).

Next, the transmit focus of the ultrasonic waves transmitted from the ultrasonic probe 10 is changed from No. 1 to No. 2 (S28, S30). Then, the steps from S12 to S26 are performed in the same manner as described above and a true focal position F2 of the ultrasonic waves corresponding to the transmit focus No. 2 is obtained (S26)

Then, the steps from S12 to S26 are performed with respect to each of the transmit focuses No. 3 to No. 8 in the same manner as described above and true focal positions F3 to F8 corresponding to the transmit focuses No. 3 to No. 8 are obtained.

Figure 8:
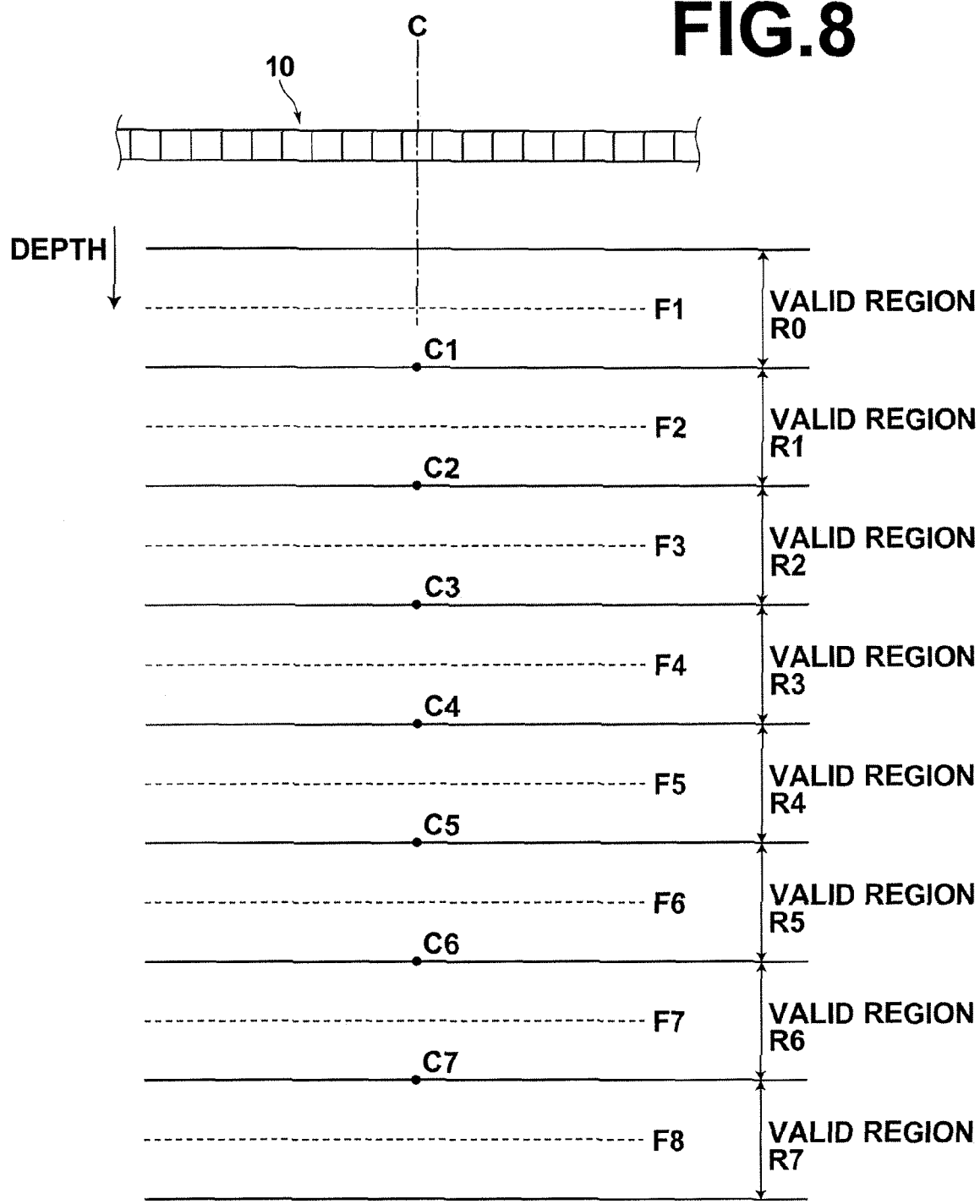
FIG. 8 schematically illustrates a valid region determined by an embodiment of the ultrasonic diagnostic apparatus of the present invention.

Then, the focal point information determination section 22 determines a valid region corresponding to each transmit focus based on the obtained true focal positions F1 to F8 of the ultrasonic waves obtained in the manner described above. More specifically, midpoints C1 to C7 between each of the focal positions F1 to F8 are obtained and regions between each of the midpoints are determined as the valid regions, as illustrated in FIG. 8. That is, the region between the midpoints C1 and C2 is determined as a valid region R1 corresponding to the transmit focus No. 2, the region between the midpoints C2 and C3 is determined as a valid region R2 corresponding to the transmit focus No. 3, the region between the midpoints C3 and C4 is determined as a valid region R3 corresponding to the transmit focus No. 4, the region between the midpoints C4 and C5 is determined as a valid region R4 corresponding to the transmit focus No. 5, the region between the midpoints C5 and C6 is determined as a valid region R5 corresponding to the transmit focus No. 6, and the region between the midpoints C6 and C7 is determined as a valid region R6 corresponding to the transmit focus No. 7. The valid region R0 shown in FIG. 8 is determined as a range obtained by doubling the depth between the focal position F1 and the midpoint C1 and the valid region R7 is determined as a range obtained by doubling the depth between the focal position F8 and the midpoint C7.

Note that all the valid regions are schematically depicted as having the same depth in FIG. 8 for the purpose of explanation, but, in actuality, these depths may possibly differ from each other.

Then, the focal point information determination section 22 outputs the information of the focal positions or valid regions determined in the manner described above to the ambient sound velocity obtaining section 24. The ambient sound velocity obtaining section 24 obtains an ambient sound velocity of the subject at the attention point specified by the operator based on the inputted information of the focus positions or valid regions. More specifically, for example, if the attention point specified by the operator is a point present in the depth of the valid region R2, an ultrasonic image signal with respect to each sound velocity setting obtained when the transmit focus is No. 3 is obtained, then an image intensity distribution of a predetermined line width and a predetermined depth width centered on the attention point is obtained with respect to each sound velocity setting, and the sound velocity setting where the sum of the image intensities becomes maximum is obtained as the ambient sound velocity of the attention point. By way of example, the predetermined depth width is 3 mm to 4 mm.

In the case where the predetermined depth width extends to valid regions of a plurality of transmit focuses, from the ultrasonic image signal of each valid region obtained at the transmit focus number corresponding to each valid region with respect to each sound velocity setting, image intensity distributions fall with in the predetermined depth width are added and a sound velocity setting where the sum becomes maximal is obtained as the ambient sound velocity of the attention point.

Then, the information of the ambient sound velocity obtained by the ambient sound velocity obtaining section 24 is outputted to the display image generation section 26 and the display image generation section 26 generates a display control signal representing a value of the inputted ambient sound velocity and outputs the generated signal to the monitor 28. The monitor 28 display the value of the ambient sound velocity of the attention point based on the inputted display control signal.

In the case where the attention point specified by the operator is within the range from the line No. 1 to line No. 17, the ambient sound velocity of the attention point may be obtained by obtaining the ultrasonic image signal of each sound velocity setting already obtained in the manner described above and based on the ultrasonic image signals as described above. In the case where the attention point is outside of the range of the line No. 1 to line No. 17, the ambient sound velocity is obtained in the following mariner.

First, in the case where an attention region centered on the attention point specified by the operator is in the valid region R2, the ambient sound velocity obtaining section 24 reads out the receive signal corresponding to each ultrasonic transducer obtained by the receiving control section 18 when the transmit focus is No. 3.

Then, the ambient sound velocity obtaining section 24 performs receive focusing on the readout receive signals with the points within an attention range of 17 lines with a depth of 3 mm to 4 mm as focuses to generate ultrasonic image signals within the attention range. Then, the ambient sound velocity obtaining section 24 performs the receive focusing using the receive delay times based on each of the sound velocity settings of 1400 m/s to 1650 m/s and generates ultrasonic image signals within the attention range with respect to each sound velocity setting.

Then, the ambient sound velocity obtaining section 24 obtains the sum of the ultrasonic image signals within the attention range with respect to each sound velocity setting and obtains a sound velocity setting where the sum with respect to each sound velocity setting becomes maximal as the ambient sound velocity of the attention point.

In the case where the attention range centered on the attention point extend a plurality of valid regions, each receive signal obtained at a transmit focus corresponding to each valid region is read out and receive focusing is performed on the receive signals with points within the attention range of each valid region as focuses to generate ultrasonic image signals within the attention range of each valid region. Then, the ultrasonic image signals within the attention range of each valid region are added and a sound velocity setting where the value of the sum with respect to each sound velocity setting becomes maximal is obtained as the ambient sound velocity of the attention point.

Although the ambient sound velocity is obtained using the sum of the ultrasonic image signals within the attention range with respect to each sound velocity setting here, the index value for obtaining the ambient sound velocity is not limited to the sum. For example, a spatial frequency spectrum of the ultrasonic image signals within the attention range may be obtained with respect to each sound velocity setting and the ambient sound velocity may be obtained based on the half width thereof. Any known index value based on the image intensity and spatial frequency spectrum may be used for obtaining the ambient sound velocity.

Further, in the embodiment described above, each time a transmit focus position is set, the true focal position with respect to the transmit focus position is obtained, but the method is not limited to this, and all the receive signals at each focus position may be obtained in advance and then the true focal position with respect to each transmit focus position may be obtained. The acquisition of the receive signals continuously in a short time at each transmit focus position may reduce errors due to movement of the subject.

Further, in the embodiment described above, an attention point is received from the operator while an ultrasonic image in a subject is displayed, and the focus position or valid region is determined and the ambient sound velocity is obtained based on the determined focus position or valid region from the time when the attention point is received. But, the method is not limited to this and, for example, the focus positions or valid regions may be obtained prior to performing an ultrasonic image diagnosis and receive signals corresponding to the focus positions or valid regions may be stored in advance, and the ambient sound velocity may be obtained based on the preset contents. In this case, the method of determining focus positions or valid regions and the method of obtaining the ambient sound velocity are identical to those described above. In the present embodiment, the focal point information determination section 22 corresponds to the focal point information setting section recited in claim 20.

Still further, in the embodiment described above, the ambient sound velocity of the attention point is obtained based on the focus position or valid region determined by the focal point information determination section 22 and the obtained ambient sound velocity is displayed as numerical value information. But, with respect to each of multiple attention points set according to each coordinate of an ultrasonic image, an ambient sound velocity may be determined based on the focal position or valid region determined by the focal point information determination section 22 and receive focusing may be performed with each coordinate corresponding to each attention point as the focal point based on the obtained ambient sound velocity, thereby generating an ultrasonic image.

Figure 11:
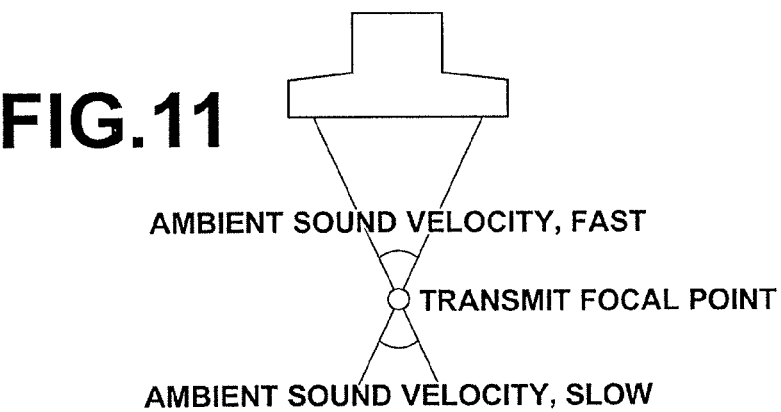
FIG. 11 illustrates the relationship between the transmit focal point and ambient sound velocity.
Figure 12:
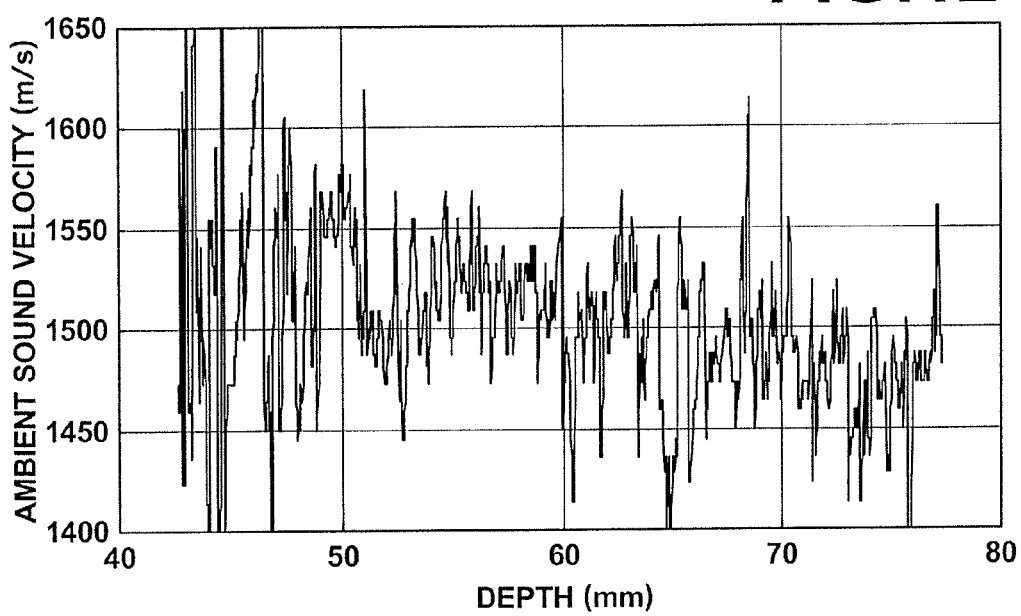
FIG. 12 illustrates an example of difference in ambient sound velocity with respect to depth.

In this case, the receive signals to be subjected to receive focusing are desirable to be those obtained at the transmit focus corresponding to the valid region in which the focal point thereof belongs. At the boundary between valid regions, however, a discontinuity occurs due to changing the receive signal used. For example, in the case where the ambient sound velocity is changed by interference even if the focal point is adjacent to the transmit focal point shown in FIG. 11, the discontinuity at the boundary is significant.

Consequently, for example, receive focusing is performed on two receive signals obtained at two transmit focus numbers forming transmit focal points sandwiching each coordinate with the coordinate as the focal point to generate two ultrasonic images and the images may be combined, for example, by weighting according to the distance between the receive focal point and each of the two transmit focal points sandwiching the receive focal point or the distance between the receive focal point and each valid region.

Figure 9:
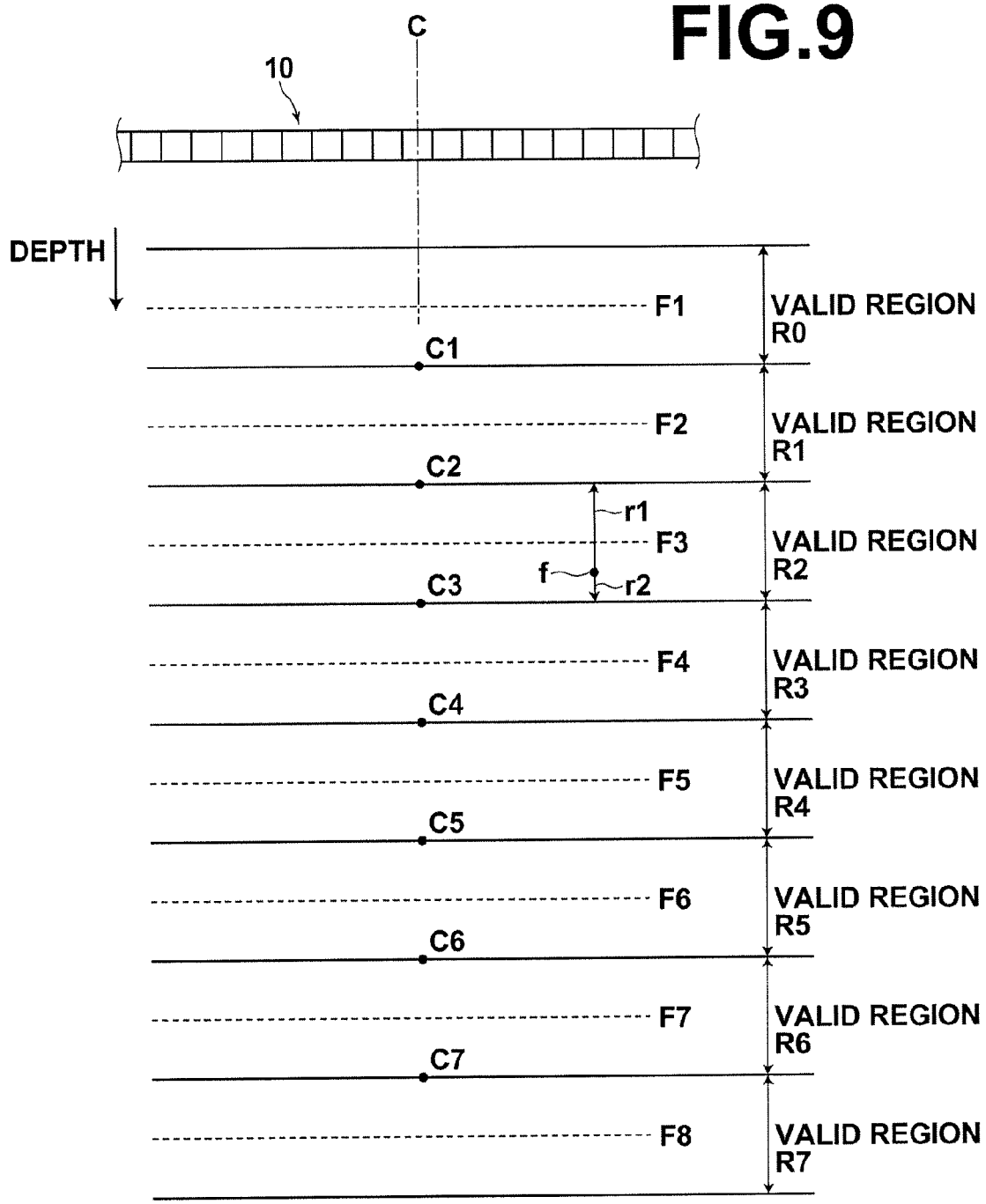
FIG. 9 is a drawing, illustrating a receive focal point f and distances r1 and r2 from the receive focal point f to each boarder of the valid region thereof.

As for the distance between the receive focal point and each valid region, for example, in the case where the receive focal point f is at the position shown in FIG. 9, the distance r1 from the boundary between the valid region R2 in which the receive focal point f belongs and the adjacent valid region R1 to the receive focal point f, and the distance r2 from the boundary between the valid region R2 in which the receive focal point f belongs and the adjacent valid region R3 to the receive focal point f may be used. But the method for setting the distance between the receive focal point and each valid region is not limited to that described above and, for example, a transition boundary, instead of the boundary, may be provided at an inner side of the boundary (for example, a position at 0.8 times the valid region) and the distance between the transition boundary and the receive focal point may be used as the distance between the receive focal point and valid region.

The method for obtaining the ambient sound velocity is not limited to that of the embodiment described above. For example, a high accurate ambient sound velocity may be obtained based on the true focal position of each transmit focus in the following manner.

Figure 10:
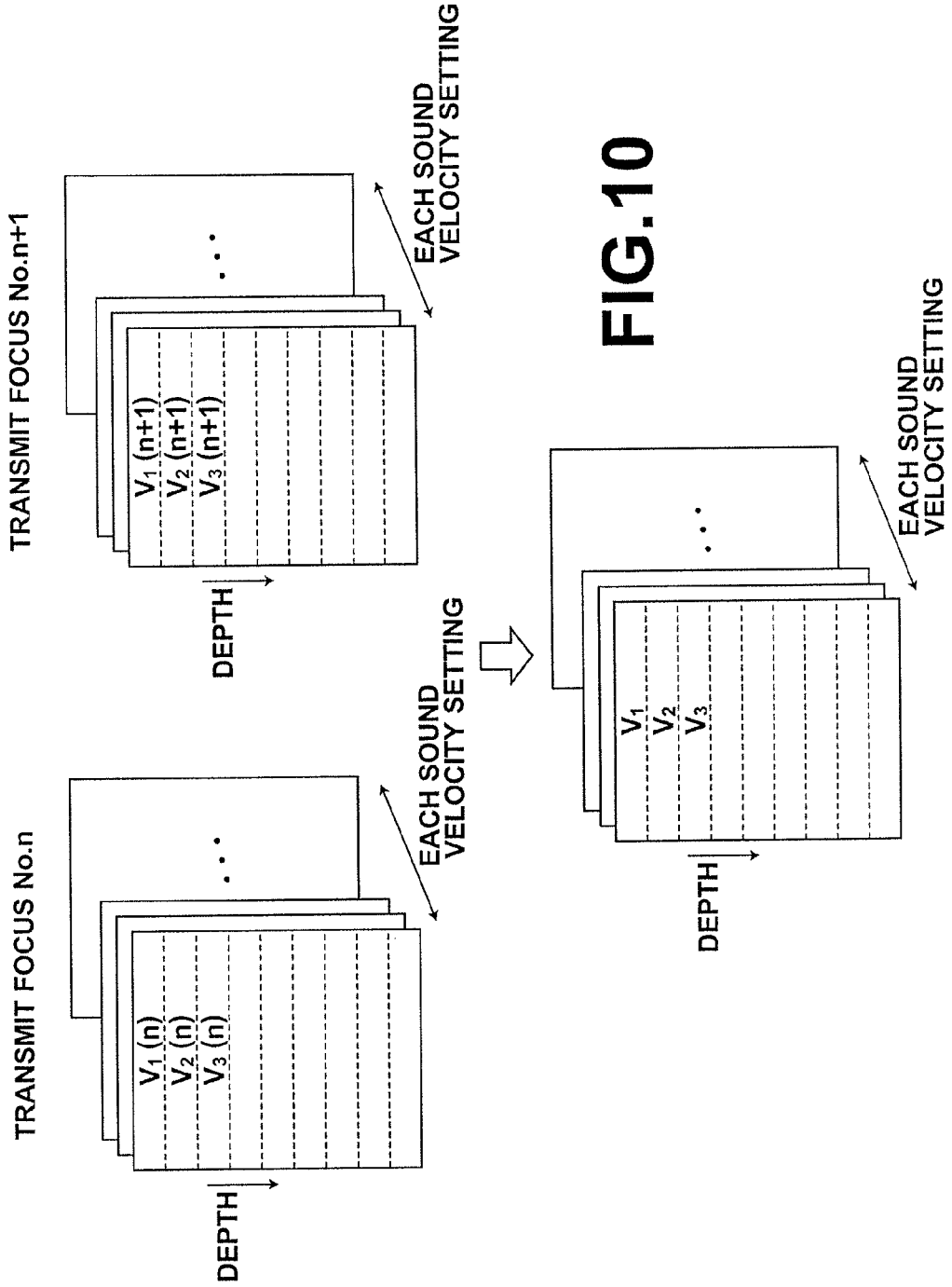
FIG. 10 illustrates an example ambient sound velocity obtaining method.

For example, with respect to an attention point, receive focusing is performed on each of two receive signals obtained at two transmit focuses, No. n and No. n+1, forming transmit focal points sandwiching the attention point based on each sound velocity setting to generate an ultrasonic image signal within the attention range centered on the attention point and, with respect to each unit depth, index values V1(n), V2(n), V3(n), . . . , and V1(n+1), V2(n+1), V3(n+1), . . . are calculated, as illustrated in FIG. 10. Then, with respect to each sound velocity setting, values V1, V2, V3, . . . which are values obtained by adding the index values of each depth obtained from the two ultrasonic images according to the distance between the depth and each of the two transmit focal points or the distance between the depth and each of the valid regions as the index value of each depth. Then the ambient sound velocity may be obtained by calculating an index value obtained by the addition of index values within the attention range with respect to each sound velocity setting and making comparison between the index values. Note that the distance between the depth and each valid region is based on the same idea as that of the distance between the receive focal point and the valid region.

If the distances from the depth to the valid regions are taken as r1, r2, the index values V1, V2, . . . may be calculated based on the formula given below.

$$V=\{V(n)+f(r1)\times V(n-1)+f(r2)\times V(n+1)\}/(1+f(r1)+f(r2))$$

where, f(r1) and f(r2) are functions that take a value of less than one which approaches zero as r1 and r2 increases respectively.

In this way, in the case where the true focal position for each transmit focus is known, a high accurate ambient sound velocity may be obtained for an attention point by combining index values calculated from ultrasonic images generated from receive signals obtained at transmit focuses forming transmit focal points sandwiching the attention point. Here, values to be combined are not limited to the index values, and receive signals themselves or provisional ambient sound velocity with respect to each unit depth shown in FIG. 6 calculated in the embodiment described above may be used. Otherwise, a provisional ambient sound velocity obtained based on ultrasonic image signals of a predetermined line width and depth width centered on the attention point may be used, instead of the provisional ambient sound velocity with respect to each unit depth. For example, in the case where the attention point is sandwiched by transmit focus No. n and transmit focus No. n+1, ultrasonic images of a predetermined line width and depth width centered on the attention point are generated with respect to each sound velocity setting using receive signals at the transmit focus No. n and receive signals at the transmit focus No. n+1. Then, for example, a sound velocity setting of an ultrasonic image among those with respect to each sound velocity setting where the sum of pixel values becomes maximal is set to the provisional ambient sound velocity to obtain the provisional ambient sound velocity corresponding to the transmit focus No. n and the provisional ambient sound velocity corresponding to the transmit focus No. n+1. Then the true ambient sound velocity may be obtained, for example, by weighed addition of the provisional ambient sound velocities according to the distance from the attention point to the transmit focus No. n and the distance from the attention point to the transmit focus No. n+1.

Further, the ambient sound velocity may be obtained by the following method.

Under a preset provisional sound velocity, each transmit focus is set so as to form a focal point at predetermined position of a subject. Thus, the true ambient sound velocity of the subject may be obtained from the difference between the preset position and true focal position.

For example, assuming the case where the transmit delay times are set by presetting the provisional sound velocity and focal position to 1540 m/s and 20 mm respectively. If the true ambient sound velocity is faster than 1540 m/s, the true focal position formed by the transmit delay times is shallower than 20 mm. In addition, as the receiving time of a reflection wave from the true focal position is a time obtained by dividing the round-trip distance to and from the true focal position by the true ambient sound velocity, the position calculated from the receiving time with the assumed ambient sound velocity of 1540 m/s is further shallower. In this way, if the true ambient sound velocity of a subject is faster than 1540 m/s, the true focal position becomes shallower than 20 mm and the position in the ultrasonic image generated by the receive signal becomes further shallower.

Conversely, if the true ambient sound velocity is slower than 1540 m/s, the true focal position is deeper than 20 mm, and the position in the ultrasonic image formed by the receive signals becomes further deeper. By leveraging this fact, the true ambient sound velocity may be obtained from the difference between the preset focal position and true focal position. For example, in the case where the true focal position in an ultrasonic image generated from the receive signal of a reflection wave from the focal point formed by driving each element at transmit delay times set with the ambient sound velocity and focal position to 1540 and 30 mm respectively is 27 mm, the true ambient sound velocity may be obtained in the following manner.

First, the depth of focal point is converted to the ultrasonic wave propagation time. More specifically, as the focal position in the ultrasonic image generated with the assumed sound velocity 1540 m/s is 27 mm, the propagation time [s] is obtained by 27[mm]/1540000[mm/s].

Next, the transmit delay of each element is obtained. The transmit delay of each element for forming the focal point at the position of 30 mm at 1540 m/s is uniquely determined.

Then, the ultrasonic wave propagation time from the focal point to each element is obtained. More specifically, the ultrasonic wave propagation time from the focal point to each element is obtained based on the ultrasonic wave propagation time and transmit delay of each element obtained above.

Then, an assumed ambient sound velocity is set and a provisional ultrasonic wave propagation time from the focal point to each element is obtained based on the assumed ambient sound velocity, and a provisional ambient sound velocity where the difference between the provisional ultrasonic wave propagation time and the ultrasonic wave propagation time from the focal point to each element obtained above becomes minimal is obtained as the true ambient sound velocity.

By the steps described above, a velocity of about 1620 m/s may be obtained as the true ambient sound velocity. In the present method, only the true ambient sound velocity at the true focal position may be obtained. For any attention point, the true ambient sound velocity may be obtained by allocating the true ambient sound velocity of an adjacent true focal position or through interpolation.

The invention claimed is:

1. A focal point information determination method which uses an ultrasonic probe having a plurality of elements disposed therein, each for transmitting an ultrasonic wave into a subject and outputting a receive signal by receiving a reflection wave reflected from the subject by the transmission of the ultrasonic wave, wherein the method comprises:
   a transmission step for transmitting the ultrasonic wave focused on a predetermined transmit focus position by driving each of the elements of the ultrasonic probe based on a predetermined transmit delay time; and
   a determination step for determining a true focal position of the ultrasonic wave transmitted to the transmit focus position or a focal point valid region that includes the true focal position based on a receive signal received by each element according to a reflection wave reflected by the transmission of the ultrasonic wave to the transmit focus position; wherein the determination step comprises the steps of:
   performing receive focusing on the receive signals corresponding to the transmit focus position using receive delay times calculated based on a plurality of sound velocity settings to obtain line image signals extending in a depth direction of the subject with respect to each of the sound velocity settings;
   obtaining a maximum image signal for each of the sound velocity settings at each depth, based on the obtained line image signals with respect to each of the sound velocity settings;
   calculating a provisional ambient sound velocity by designating the sound velocity setting employed when the maximum image signal is obtained;
   obtaining a provisional ambient sound velocity distribution that includes calculated provisional ambient sound velocities at each depth of the subject; and
   determining the true focal position or the focal point valid region based on the obtained provisional ambient sound velocity distribution, wherein
   the true focal position or the focal point valid region is determined based on a depth at which a variation of the provisional ambient sound velocity distribution becomes minimal compared to the variations of the provisional ambient sound velocity distribution at the other depth.

2. The focal point information determination method of claim 1, wherein:
   the transmission step is a step in which the ultrasonic wave focused on a plurality of transmit focus positions is transmitted with respect to each transmit focus position; and
   the determination step is a step in which a true focal position of the ultrasonic wave transmitted to each transmit focus position is determined based on a receive signal received by the transmission of the ultrasonic wave to each transmit focus position.

3. An ambient sound velocity determination method for obtaining an ambient sound velocity of any arbitrary attention point in the subject based on a receive signal obtained by transmitting the ultrasonic wave to a transmit focus position corresponding to each of the plurality of true focal positions determined by the focal point information determination method of claim 2.

4. An ambient sound velocity determination method for obtaining an ambient sound velocity of any arbitrary attention point in the subject based on the true focal position or the focal point valid region that includes the true focal position determined by the focal point information determination method of claim 1.

5. An ambient sound velocity obtaining method for obtaining an ambient sound velocity of any arbitrary attention point in the subject based on the focal position or the focal point valid region that includes the true focal position determined by the focal point information determination method of claim 1,
   wherein a range of the line image signals in the depth direction used for obtaining the provisional ambient sound velocity is narrower than a range of the line image signals in the depth direction used for obtaining the ambient sound velocity.

6. A focal point information determination apparatus, comprising:

an ultrasonic probe having a plurality of elements disposed therein, each for transmitting an ultrasonic wave into a subject and outputting a receive signal by receiving a reflection wave reflected from the subject by the transmission of the ultrasonic wave;

a transmission control section for transmitting the ultrasonic wave focused on a predetermined transmit focus position by driving each of the elements of the ultrasonic probe based on a predetermined transmit delay time; and a focal point information determination section for determining a true focal position of the ultrasonic wave transmitted to the transmit focus position or a focal point valid region that includes the true focal position based on a receive signal received by each element according to a reflection wave reflected by the transmission of the ultrasonic wave to the transmit focus position, wherein:

the apparatus further comprises a receiving control section for performing receive focusing on the receive signals corresponding to the transmit focus position using receive delay times calculated based on a plurality of sound velocity settings to obtain line image signals extending in a depth direction of the subject with respect to each of the sound velocity settings;

the focal point information determination section is a section that obtains a maximum image signal for each of the sound velocity settings at each depth, based on the obtained line image signals with respect to each of the sound velocity settings, calculates a provisional ambient sound velocity by designating the sound velocity setting employed when the maximum image signal is obtained, and obtains a provisional ambient sound velocity distribution in the depth direction that includes calculated provisional ambient sound velocities at each depth of the subject, by calculating the provisional ambient sound velocities at each depth of the subject; and the focal point information determination section is a section that determines the true focal position or the focal point valid region based on a depth at which a variation of the provisional ambient sound velocity distribution becomes minimal compared to the variations of the provisional ambient sound velocity distribution at the other depth.

7. The focal point information determination apparatus of claim 6, wherein:

the transmission control section is a section that transmits the ultrasonic wave focused on a plurality of transmit focus positions with respect to each transmit focus position; and the focal point information determination section is a section that determines a true focal position of the ultrasonic wave transmitted to each of the transmit focus positions.

8. An ambient sound velocity obtaining apparatus, comprising:

the focal point information determination apparatus of claim 7; and an ambient sound velocity obtaining section for obtaining an ambient sound velocity of any arbitrary attention point in the subject based on a receive signal obtained by transmitting the ultrasonic wave to a transmit focus position corresponding to each of the plurality of true focal positions determined by the focal point information determination apparatus.

9. An ambient sound velocity obtaining apparatus, comprising:

the focal point information determination apparatus of claim 6; and an ambient sound velocity obtaining section for obtaining an ambient sound velocity of any arbitrary attention point in the subject based on the true focal position or the focal point valid region that includes the true focal position determined by the focal point information determination apparatus.

10. The ambient sound velocity obtaining apparatus of claim 9, further comprising an attention point input section for receiving an input specifying any arbitrary attention point.

11. The ambient sound velocity obtaining apparatus of claim 9, further comprising a receiving control section for generating an ultrasonic image signal using a receive delay time calculated based on the ambient sound velocity obtained by the ambient sound velocity obtaining section.

12. An ambient sound velocity obtaining apparatus, comprising:

the focal point information determination apparatus of claim 6; and an ambient sound velocity obtaining section for obtaining an ambient sound velocity of any arbitrary attention point in the subject based on the true focal position or the focal point valid region that includes the true focal position determined by the focal point information determination apparatus, wherein a range of the line image signals in the depth direction used for obtaining the provisional ambient sound velocity by the focal point information determination section is narrower than a range of the line image signals in the depth direction used for obtaining the ambient sound velocity by the ambient sound velocity obtaining section.

* * * * *